US011161866B2

(12) United States Patent
Reichelt et al.

(10) Patent No.: US 11,161,866 B2
(45) Date of Patent: Nov. 2, 2021

(54) CRYSTAL FORM OF A DITHIOLENE METAL COMPLEX

(71) Applicant: BASF SE, Ludwigshafen am Rhein (DE)

(72) Inventors: Helmut Reichelt, Ludwigshafen (DE); Hans Reichert, Basel (CH); Oliver Seeger, Ludwigshafen (DE); Korinna Dormann, Ludwigshafen (DE); Rene Fischer, Basel (CH); Christian Doerr, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/638,875

(22) PCT Filed: Sep. 18, 2018

(86) PCT No.: PCT/EP2018/075130
§ 371 (c)(1),
(2) Date: Feb. 13, 2020

(87) PCT Pub. No.: WO2019/057683
PCT Pub. Date: Mar. 28, 2019

(65) Prior Publication Data
US 2020/0190127 A1    Jun. 18, 2020

(30) Foreign Application Priority Data
Sep. 21, 2017   (EP) ..................................... 17192402

(51) Int. Cl.
| C07D 233/84 | (2006.01) |
| B42D 25/20 | (2014.01) |
| C09D 11/02 | (2014.01) |
| C07F 15/04 | (2006.01) |

(52) U.S. Cl.
CPC ............ *C07F 15/045* (2013.01); *B42D 25/20* (2014.10); *C09D 11/02* (2013.01); *C07B 2200/13* (2013.01)

(58) Field of Classification Search
CPC .. C07D 233/84; B42D 25/20; C07B 2200/13; C09D 11/02; C07F 15/045; C07F 15/04
See application file for complete search history.

(56) References Cited

U.S. PATENT DOCUMENTS

| 5,282,894 A | 2/1994 | Albert et al. |
| 2004/0207700 A1 | 10/2004 | Hall et al. |
| 2008/0241492 A1 | 10/2008 | Demartin Maeder et al. |
| 2013/0234427 A1 | 9/2013 | Reichelt et al. |

FOREIGN PATENT DOCUMENTS

| EP | 2 942 378 A1 | 11/2015 |
| EP | 3 067 216 A1 | 9/2016 |
| EP | 3 078 503 A1 | 10/2016 |
| JP | 2003-262953 A | 9/2003 |
| JP | 2004-45653 A | 2/2004 |
| JP | 2005-99755 A | 4/2005 |
| WO | WO 2007/091094 A1 | 8/2007 |
| WO | WO 2007/132214 A1 | 11/2007 |
| WO | WO 2008/086931 A1 | 7/2008 |
| WO | WO 2012/069518 A1 | 5/2012 |
| WO | WO 2012/152584 A1 | 11/2012 |

OTHER PUBLICATIONS

International Search Report dated Oct. 19, 2018 in PCT/EP2018/075130, 4 pages.
International Preliminary Report on Patentability dated Mar. 24, 2020 in PCT/EP2018/075130 filed Sep. 18, 2018, 6 pages.
Extended European Search Report dated Dec. 7, 2017 in Patent Application No. 17192402.0, 3 pages.
M.Carla Aragoni, et al., "NIR Dyes Based on (M(R.R'timdt)2) Metal-Dithiolenes: Additivity of M, R, and R' Contributions to Tune the NIR Absorption (M = Ni, Pd, Pt; R,R'timdt = Monoreduced Form of Disubstituted Imidazolidine-2,4,5-Trithione)" European Journal of Inorganic Chemistry, vol. 2003, No. 10, XP007904536, May 2003, pp. 1939-1947.
Massimiliano Area, et al., "Synthesis, X-ray Crystal Structure and Spectroscopic Characterization of the New Dithiolene [Pd(Et2timdt)2] and of its Adduct with Molecular Diiodine [Pd(Et2timdt)2]·I2·CHCl3 (Et2timdt = Monoanion of 1,3-Diethylimidazolidine-2,4,5-Trithione)" Journal of the Chemical Society, Dalton Transactions, Issue 2, 1998, pp. 3731-3736.
U.S. Appl. No. 16/482,582, filed Jul. 31, 2019, US 2020/0010680 A1, Martin Weber, et al.

*Primary Examiner* — Sun Jae Yoo
(74) *Attorney, Agent, or Firm* — Faegre Drinker Biddle & Reath LLP

(57) ABSTRACT

The present invention relates to a new crystal form of bis(diphenylimidazolidinetrithione-κS4, κS5)-, (SP-4-1)-nickel(II), a printing ink formulation for security printing and security documents, comprising the new crystal form of bis(diphenylimidazolidinetrithione-κS4, κS5)-, (SP-4-1)-nickel(II) as well as its use as IR absorber.

12 Claims, 2 Drawing Sheets

X-ray diffraction (PXRD) pattern of Form A of compound (1) described in WO2012/069518

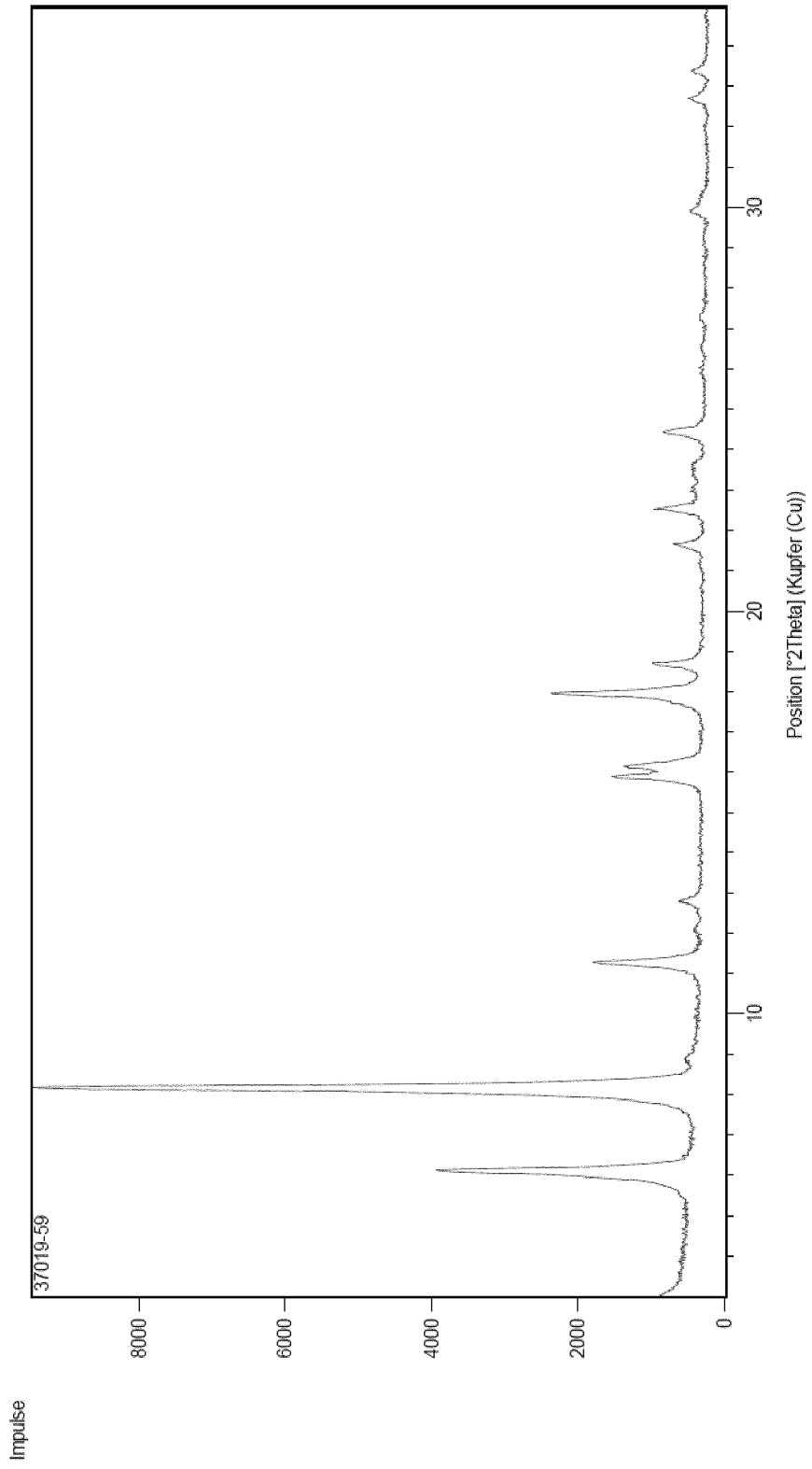

CRYSTAL FORM OF A DITHIOLENE METAL COMPLEX

The present invention relates to a new crystal form of a dithiolene metal complex, a printing ink formulation for security printing and security documents, comprising the dithiolene metal complex as well as its use as (colourless) IR absorber.

Colourless, or at least barely coloured, IR absorbers meet a significant technical need in a wide range of applications, such as security printing (bank notes, identity cards, passports, tax stamps, stock certificates, credit cards, labels etc.), invisible and/or IR readable bar codes, the laser-welding of plastics, the curing of surface-coatings using IR radiators, the drying and curing of print, the fixing of toners on paper or plastics, optical filters for PDPs (plasma display panels), laser marking e.g. of paper or plastics, the heating of plastics preforms, heat shielding applications, etc.

A large number of organic and inorganic substances belonging to different compound classes and with a great variety of different structures are known for the application as IR absorbers. Notwithstanding that large numbers of known compound classes and structures, the provision of products with a complex profile of properties often presents difficulties. There is a continuing demand for IR absorber that are "colourless" (i.e. with the minimum possible inherent colour), and that simultaneously meet the technical stability requirements (chemical stability, heat stability and/or light stability).

A special field of application for colourless IR absorbers regards inks for printing processes which are used for printing currency and other security documents, also referred to as "security printing". Typical security printing processes are processes, wherein an ink composition is employed that is designed to selectively absorb radiation in parts of the "optical infrared" spectrum, whilst being transparent in other parts of it. IR absorbers for security printing are available, for example, from "American Dye Source", but virtually all of them have a noticeable absorption in the VIS range of the spectrum (from 400 to 700 nm).

US2008/0241492 describes an intaglio printing ink for a security printing process, wherein the ink comprises a polymeric organic binder and an infrared absorbing material that comprises transition element atoms or ions whose infrared absorption is a consequence of electronic transitions within the d-shell of the transition element. Suitable transition elements are Ti, V, Cr, Mn, Fe, Co, Ni, and Cu. In a suitable embodiment, the infrared absorbing material is a glass, in which there is a coordination of the transition element ions to phosphate and/or fluoride anions present in the glass. In a further suitable embodiment, the infrared absorbing material is an IR-absorbing transition element atom or ion bound to the polymer binder of the ink. In particular, the infrared absorbing material is an IR-absorbing complex of a transition element atom or ion and a binding site contained in the polymer, e.g. an organic thiourea-copper(II) complex dissolved in the polymeric binder.

U.S. Pat. No. 5,282,894 describes a liquid useful as printing ink that contains one or more dyes with their absorption maximum within the range from 700 to 1200 nm selected from phthalocyanines, naphthalocyanines, nickel-dithiolene complexes, aminium compounds of aromatic amines, methine dyes or azulenesquaric acid dyes, as well as solvent and binder.

WO2007/091094 describes an image article that comprises a substrate having a security image coated on at least a portion thereof, wherein the security image comprises a defined infrared-absorbing compound, for example Pigment Green 8, that does not create a strongly coloured security image. The disclosed infrared-absorbing compounds still have a noticeable absorption in the VIS range of the spectrum.

WO2007/132214 describes a composition comprising an ink and an infrared-absorbing material that comprises a metal, a metal salt, a metal oxide or metal nitride, wherein the metal is in particular selected from periods 4, 5 or the lanthanides. Also described is an article comprising a substrate having imaged thereon an infrared-absorbing material to form a security image, and a method of manufacture of such an article by image-wise application of a composition comprising such an infrared-absorbing material to a substrate.

M. Arca et al. describe in J. Chem. Soc., Dalton Trans. 1998, 3731-3736 metal dithiolenes (see scheme 1) belonging to the general class $[M(R,R'timdt)_2]$ (M=Ni, Pd; (R,R'timdt)=monoanion of disubstituted imidazolidine-2,4,5-trithione; R and R'=ethyl or isopropyl). These metal dithiolenes exhibit large π delocalization being responsible for the NIR-absorption.

JP2003262953A, JP2004045653A and JP200599755A describe metal dithiolenes $[M(R,R'timdt)_2]$, wherein R and R' are selected from unsubstituted and substituted alkyl, cycloalkyl and aryl groups.

M. C. Aragoni et al. describe in Eur. J. Inorg. Chem. 2003, 1939-1947 NIR dyes based on $[M(R,R'timdt)_2]$ metal dithiolenes, wherein R and R' are inter alia selected from unsubstituted and substituted aryl groups.

WO2008/086931 teaches the use of dithiolene metal complexes $[M(L)_2]$, wherein L is the monoanion of a disubstituted imidazolidine-2-chalcogenone-4,5-dithione and the chalcogene is O or S, as colourless IR absorbers. Whereas aryl substituted compounds are mentioned in very general terms, there is no concrete teaching with regard to those compounds. In particular, in all examples the nitrogen atoms bear only unsubstituted and substituted alkyl and alkenyl groups.

US20040207700 relates to a stabilized ink composition comprising an IR-absorbing metal-dithiolene dye and a singlet oxygen quencher. The singlet oxygen quencher is selected from ascorbic acid, 1,4-diazabicyclo-[2.2.2]octane (DABCO), azides (e.g. sodium azide), histidine or tryptophan.

WO2012069518 relates to the use of specific metal complexes of dithiolenes with aryl or heteroaryl substituted imidazolidine-2-chalcogenone-4,5-dithione ligands as colourless IR absorbers.

WO2012152584 relates to specific metal complexes of dithiolenes with perfluoroalkyl substituted imidazolidine-2-chalcogenone-4,5-dithione ligands, a process for their preparation and their use as colourless IR absorbers, for optical filters application; especially for plasma display panels, or for laser welding of plastics.

EP2942378 relates to an inkjet ink composition comprising: at least one near infrared (NIR) absorbent selected from the group consisting of: metal dithiolene complexes, cyanines, and phthalocyanines in amount of from 0.05% to 5% w/w; gamma-butyrolactone as a solvent in amount of from 1% to 30% w/w; 2-butoxyethyl acetate as a solvent in amount of from 50% to 95% w/w; and vinylchloride-vinylacetate copolymer as a binder in amount of from 0.1% to 5% w/w.

EP3067216 relates to chromophoric compositions, in particular to compositions containing as chromophore an IR absorbing compound and specific stabilizing compounds which prevent the oxidative degradation of the chromophore.

EP3078503A1 relates to a security document including a transparent window, wherein an infrared absorbing material is applied to or incorporated within the window, wherein the infrared absorbing material comprises an infrared absorbing dye, and infrared absorbing nanoparticles having an average size of not greater than 100 nm, and wherein the infrared absorbing material is substantially transparent to visible radiation. The infrared absorbing dye is an organic or complexed dye, or a perylene-based or dithiolene-based dye, or is selected from a group including Lumogen 765 and Lumogen 788.

A new crystal form of bis(diphenylimidazolidinetrithione-κS4, κS5)-, (SP-4-1)-nickel(II) (Form B of compound (1)) has been found, surprisingly, which is thermally more stable than Form A of compound (1) described in WO2012/069518. The new crystal form of compound (1) can be advantageously employed as IR absorber for security printing and the laser-welding of plastics. Due to its unique application properties, such as, for example, high resistance against chemicals and solvents, colourlessness, good light stability and good thermal stability, it is in particular suitable as IR absorber for security printing, especially for bank notes, identity cards, passports, tax stamps, stock certificates, credit cards, labels etc.

SUMMARY OF THE INVENTION

In a first aspect, the invention provides a new crystal form of bis(diphenylimidazolidinetrithione-κS4, κS5)-, (SP-4-1)-nickel(II) (compound (1)), characterized in an X-ray diffraction pattern by diffraction peaks corresponding to two theta scattering angles of 6.1; 8.2; 11.3; 15.9; 16.1 and 17.9.

The x-ray diffraction patterns are measured with Cu-$K_{alpha}$ radiation. It will be understood that the d-value and the scattering angle (two theta) are, of course, subject to fluctuation due to experimental error of +/−0.2 (scattering angle).

The crystal form of compound (1) is more stable than a crystal form of compound (1) (Form A of compound (1)) which is characterized in an X-ray diffraction pattern by diffraction peaks corresponding to two theta scattering angles of 7.4; 8.0 and 18.3.

In a further aspect, the invention provides a printing ink formulation for security printing, comprising the new crystal form of compound (1) as defined above and in the following.

In a further aspect, the invention provides a security document, comprising a substrate and the new crystal form of compound (1) as defined above and in the following.

In a further aspect, the invention provides a security document, obtainable by a printing process, wherein a printing ink formulation is employed that comprises the new crystal form of compound (1) as defined above and in the following.

In a further aspect, the invention provides the use of the new crystal form of compound (1) as colourless IR absorber.

In a further aspect, the invention provides a method of detecting a genuine security document by measuring the spectra of the colourless IR absorber.

FIG. 2 depicts the PXRD pattern of Form B of Compound (1) according to the present invention.

Figure 1:
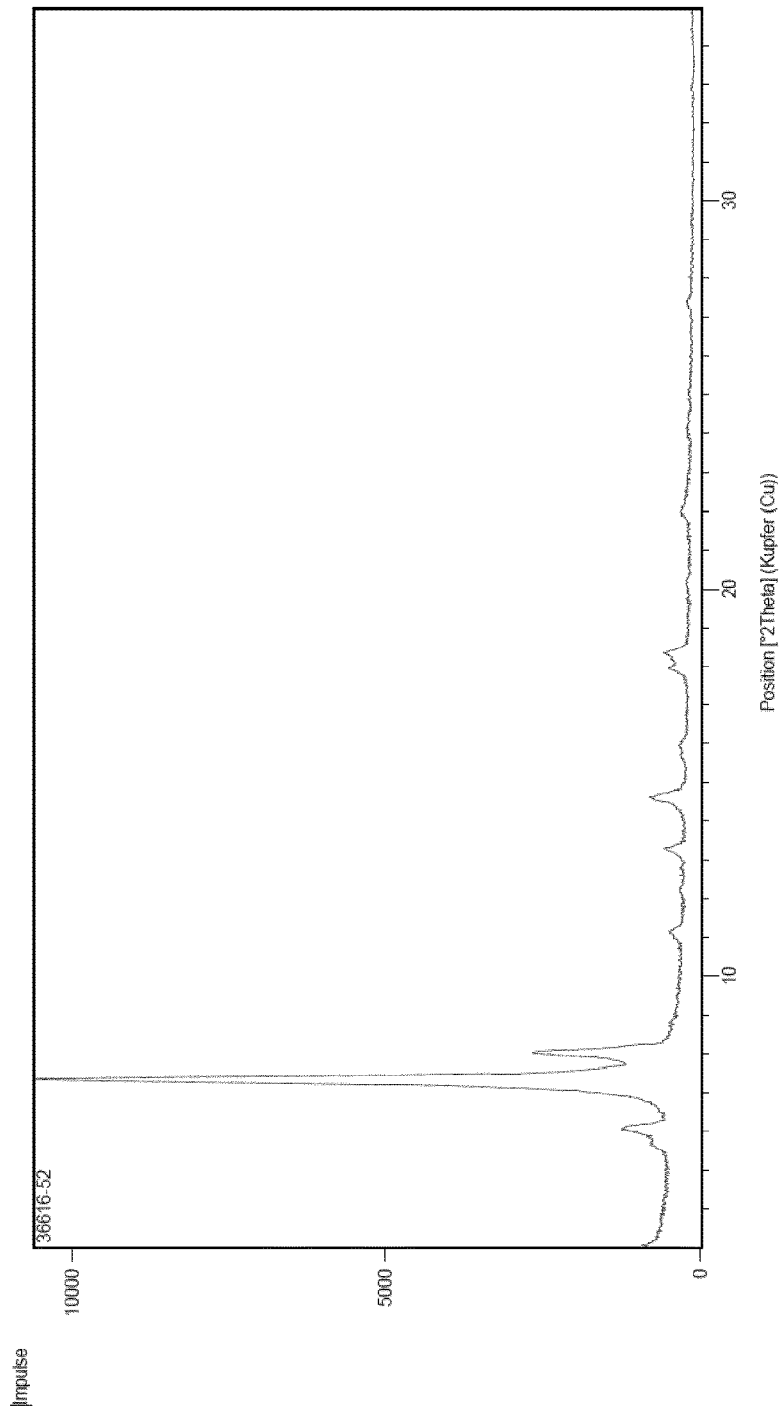
FIG. 1 shows the powder X-ray diffraction (PXRD) pattern of Form A of compound (1) described in WO2012/069518.

The new crystal form of compound (1) is characterized by the PXRD pattern shown in FIG. 2.

In general, the compound (1) has at least one of the following advantageous properties:
- good fastness to chemicals, in particular fastness to bleaching with hypochlorite and fastness to solvents (like toluene, acetone or dichloromethane),
- good fastness to boiling water,
- good fastness to light,
- colourlessness (i.e. minimal absorption in the VIS range of the spectrum (from 400 to 700 nm))
- good heat stability,
- high compatibility with a multiplicity of formulations, in particular printing ink formulations used in security printing and thermoplastic polymer formulations used for laser-welding.

The new crystal form of compound (1) (Form B of compound (1)) is thermally more stable than Form A of compound (1) described in WO2012/069518. As shown in Example 2 of the present application Form B of compound (1) is the thermodynamic stable form and, hence, is characterized by improved process stability (no problem for higher temperature handling), processability, reproducibility and storage stability in comparison to Form A of compound (1). Due to the production process Form B of compound (1) has a lower tendency to agglomerate and, hence, is easier to dose.

The new crystal form of the compound of formula (1) according to the present invention can be produced
- by heating a crystal form of the compound of formula (1), which is characterized in an X-ray diffraction pattern by diffraction peaks corresponding to two theta scattering angles of 7.4; 8.0 and 18.3, at 150° C. for 12 hours; or
- by heating a suspension of the crystal form of the compound of formula (1), which is characterized in an X-ray diffraction pattern by diffraction peaks corresponding to two theta scattering angles of 7.4; 8.0 and 18.3, in a solvent at reflux for 5 minutes to 12 hours.

If chlorobenzene is used as solvent, the suspension is refluxed for 2 hours. If 3-methoxypropanenitrile is used as solvent, the suspension is refluxed for ¼ hours. Reference is made to the Examples of the present application.

The new crystal form of compound (1) can be used inter alia for security printing, invisible and/or IR readable bar codes, the laser-welding of plastics, the curing of surface-coatings using IR radiators, the drying and curing of print, the fixing of toners on paper or plastics, optical filters for plasma display panels, laser marking of paper or plastics, the heating of plastics preforms, in 3D printing, in optical sensors and for heat shielding applications.

The new crystal form of compound (1) can also be used in the form of a mixture, comprising new crystal form of compound (1) and at least one further IR absorber different from the new crystal form of compound (1). Suitable further IR absorbers are in principle all known classes of IR absorbers that are compatible with the new crystal form of compound (1). Preferred further IR absorbers are selected from polymethines, phthalocyanines, naphthalocyanines, quinone-diimmonium salts, aminium salts, rylenes, inorganic IR absorbers and mixtures thereof. Further polymethine IR absorbers are preferably selected from cyanines, squaraines, croconaines and mixtures thereof. Further inorganic IR absorbers are preferably selected from indium tin oxide, antimony tin oxide, lanthanum hexaboride, tungsten bronzes, copper salts etc.

The IR absorbers can be generally used in a concentration of from 10 ppm to 25%, preferably 100 ppm to 10%, depending on the chosen application.

The new crystal form of compound (1) and IR absorber mixtures are especially suitable for security printing.

Security printing is the field that deals with the printing of items such as currency, passports, tamper-evident labels, stock certificates, postage stamps, identity cards, etc. The main goal of security printing is to prevent forgery, tampering or counterfeiting.

In the field of automated banknote processing, IR-absorption plays an important role. Most of the actually circulating currency carries not only visibly coloured printings, but also specific features which are only detectable in the infrared part of the spectrum. Generally, these IR-features are implemented for use by automatic currency processing equipment, in banking and vending applications (automatic teller machines, automatic vending machines, etc.), in order to recognize a determined currency bill and to verify its authenticity, in particular to discriminate it from replicas made by colour copiers.

Accordingly, the present invention also relates to a method of detecting the authenticity of a security document as defined above, or below, comprising the steps of:
  a) measuring an absorbance, reflectance or transmittance spectrum of the security document in the VIS/NIR range of the electromagnetic spectrum; and
  b) comparing the spectrum measured under a) and/or information derived therefrom with a corresponding spectrum and/or information of an authentic security element.

All security documents are required to have good stability and durability. In the case of bank notes, these requirements are extreme, as bank notes are subjected to toughest use conditions by the public—they are subjected to material stress by folding, crumpling etc., subjected to abrasion, exposed to weather, exposed to bodily fluids such as perspiration, laundered, dry-cleaned, ironed etc. —and, after having been subjected to this, are expected to be as legible as when they started. Furthermore, it is essential that the documents nevertheless should have a reasonable life time, ideally of some years, despite suffering the afore-mentioned conditions. During this time, the documents, and thus the inks on them (including invisible security markings), should be resistant to fading or colour change. Hence, any ink used in a security printing process should, when cured, be robust, water-resistant, resistant to various chemicals and flexible. Moreover, as certain states are moving away from the use of paper as the substrate for bank notes, the employed printing ink formulations should be useable on plastics as well as paper. The new crystal form of compound (1) because of its unique application properties is especially suitable for printing ink formulations that are employed for security printing and in particular for bank notes, identity cards, passports, tax stamps, stock certificates, credit cards, labels etc.

In security printing, the IR absorber is added to a printing ink formulation. Suitable printing inks are water-based, oil-based or solvent-based printing inks, based on pigment or dye, for inkjet printing, gravure printing, flexographic printing, screen printing, intaglio printing, offset printing, laser printing or letterpress printing and for use in electrophotography. Printing inks for these printing processes usually comprise solvents, binders, and also various additives, such as plasticizers, antistatic agents or waxes. Printing inks for offset printing, intaglio printing and letterpress printing are usually formulated as high-viscosity paste printing inks, whereas printing inks for inkjet printing, flexographic printing and gravure printing are usually formulated as liquid printing inks with comparatively low viscosity.

In the context of the present invention, the expression "printing ink" also encompasses formulations that in addition to at least one IR absorber of the general formula (I) comprise a colorant. The expression "printing ink" also encompasses printing lacquers that comprise no colorant.

The printing ink formulation for security printing according to the invention preferably comprises
a) the new crystal form of compound (1) as defined above,
b) a polymeric binder,
c) a solvent,
d) optionally at least one colorant, and
e) optionally at least one further additive.

Suitable components of printing inks are conventional and are well known to those skilled in the art. Examples of such components are described in "Printing Ink Manual", fourth edition, Leach R. H. et al. (eds.), Van Nostrand Reinhold, Wokingham, (1988). Details of printing inks and their formulation are also disclosed in "Printing Inks"-Ullmann's Encyclopedia of Industrial Chemistry, Sixth Edition, 1999 Electronic Release. A formulation of an IR-absorbing intaglio ink formulation is described in US 20080241492 A1. The disclosure of the afore-mentioned documents is incorporated herein by reference.

The printing ink formulation according to the invention contains in general from 0.0001 to 25% by weight, preferably from 0.001 to 15% by weight, in particular from 0.01 to 5% by weight, based on the total weight of the printing ink formulation, of component a).

The new crystal form of compound (1) is present in the printing ink formulation in dissolved form or in solid form (in a finely divided state).

The printing ink formulation according to the invention contains in general from 5 to 74% by weight, preferably from 10 to 60% by weight, more preferably from 15 to 40% by weight, based on the total weight of the printing ink formulation, of component b).

Suitable polymeric binders b) for the printing ink formulation according to the invention are for example selected from natural resins, phenol resin, phenol-modified resins, alkyd resins, polystyrene homo- and copolymers, terpene resins, silicone resins, polyurethane resins, urea-formaldehyde resins, melamine resins, polyamide resins, polyacrylates, polymethacrylates, chlorinated rubber, vinyl ester resins, acrylic resins, epoxy resins, nitrocellulose, hydrocarbon resins, cellulose acetate, and mixtures thereof.

The printing ink formulation according to the invention can also comprise components that form a polymeric binder by a curing process. Thus, the printing ink formulation according to the invention can also be formulated to be energy-curable, e.g. able to be cured by UV light or EB (electron beam) radiation. In this embodiment, the binder comprises one or more curable monomers and/or oligomers. Corresponding formulations are known in the art and can be found in standard textbooks such as the series "Chemistry & Technology of UV & EB Formulation for Coatings, Inks & Paints", published in 7 volumes in 1997-1998 by John Wiley & Sons in association with SITA Technology Limited.

Suitable monomers and oligomers (also referred to as prepolymers) include epoxy acrylates, acrylated oils, urethane acrylates, polyester acrylates, silicone acrylates, acrylated amines, and acrylic saturated resins. Further details and examples are given in "Chemistry & Technology of UV & EB Formulation for Coatings, Inks & Paints", Volume II: Prepolymers & Reactive Diluents, edited by G Webster.

If a curable polymeric binder is employed, it may contain reactive diluents, i.e. monomers which act as a solvent and which upon curing are incorporated into the polymeric binder. Reactive monomers are typically chosen from acrylates or methacrylates, and can be monofunctional or multifunctional. Examples of multifunctional monomers include polyester acrylates or methacrylates, polyol acrylates or methacrylates, and polyether acrylates or methacrylates.

In the case of printing ink formulations to be cured by UV radiation, it is usually necessary to include at least one photoinitiator to initiate the curing reaction of the monomers upon exposure to UV radiation. Examples of useful photoinitiators can be found in standard textbooks such as "Chemistry & Technology of UV & EB Formulation for Coatings, Inks & Paints", Volume III, "Photoinitiators for Free Radical Cationic and Anionic Polymerisation", 2nd edition, by J. V. Crivello & K. Dietliker, edited by G. Bradley and published in 1998 by John Wiley & Sons in association with SITA Technology Limited. It may also be advantageous to include a sensitizer in conjunction with the photoinitiator in order to achieve efficient curing.

The printing ink formulation according to the invention contains in general from 1 to 94.9999% by weight, preferably from 5 to 90% by weight, in particular from 10 to 85% by weight, based on the total weight of the printing ink formulation, of a solvent c).

Suitable solvents are selected from water, organic solvents and mixtures thereof. For the purpose of the invention, reactive monomers which also act as solvents are regarded as part of the afore-mentioned binder component b).

Examples of solvents comprise water; alcohols, e.g. ethanol, 1-propanol, 2-propanol, ethylene glycol, propylene glycol, diethylene glycol and ethoxy propanol; esters, e.g. ethyl acetate, isopropyl acetate, n-propyl acetate and n-butyl acetate; hydrocarbons, e.g. toluene, xylene, mineral oils and vegetable oils, and mixtures thereof.

The printing ink formulation according to the invention may contain an additional colorant d). Preferably, the printing ink formulation contains from 0 to 25% by weight, more preferably from 0.1 to 20% by weight, in particular from 1 to 15% by weight, based on the total weight of the printing ink formulation, of a colorant d).

Suitable colorants d) are selected conventional dyes and in particular conventional pigments. The term "pigment" is used in the context of this invention comprehensively to identify all pigments and fillers, examples being colour pigments, white pigments, and inorganic fillers. These include inorganic white pigments, such as titanium dioxide, preferably in the rutile form, barium sulfate, zinc oxide, zinc sulfide, basic lead carbonate, lithopones (zinc sulfide+ barium sulfate), or coloured pigments, examples being iron oxides, bismuth vanadates, lead chromates, lead molybdates, iron blue, Cobalt blue, Cobalt green, Ni-rutile yellow, Cr-rutil yellow, zinc yellow, zinc green, ultramarine, manganese black, antimony black, manganese violet, carbon black, graphite. Besides the inorganic pigments the printing ink formulation of the invention may also comprise organic colour pigments, examples being Monoazo, Disazo, ß-Naphthol, Naphthol AS, Azo pigment Lakes, Benzimidazolone, Metal complex pigments, Isoindolinone, Isoindoline, Phthalocyanine, Quinacridone, Perylene, perinone, Diketopyrrolo-Pyrrol, Thioindigo, Anthraquinone, Anthrapyrimidine, Indanthrone, Flavanthrone, Pyranthrone, Dioxazine, Triarylcarbonium, Quinophthalone. Also suitable are synthetic white pigments with air inclusions to increase the light scattering, such as the Rhopaque® dispersions. Suitable fillers are, for example, aluminosilicates, such as feldspars, silicates, such as kaolin, talc, mica, magnesite, alkaline earth metal carbonates, such as calcium carbonate, in the form for example of calcite or chalk, magnesium carbonate, dolomite, alkaline earth metal sulfates, such as calcium sulfate, silicon dioxide, etc.

The printing ink formulation according to the invention may contain at least one additive e). Preferably, the printing ink formulation contains from 0 to 25% by weight, more preferably from 0.1 to 20% by weight, in particular from 1 to 15% by weight, based on the total weight of the printing ink formulation, of at least one component e).

Suitable additives (component e)) are selected from plasticizers, waxes, siccatives, antistatic agents, chelators, antioxidants, stabilizers, adhesion promoters, surfactants, flow control agents, defoamers, biocides, thickeners, etc. and combinations thereof. These additives serve in particular for fine adjustment of the application-related properties of the printing ink, examples being adhesion, abrasion resistance, drying rate, or slip.

In particular, the printing ink formulation for security printing according to the invention preferably contains
a) 0.0001 to 25% by weight of the new crystal form of compound (1),
b) 5 to 74% by weight of at least one polymeric binder,
c) 1 to 94.9999% by weight of at least one a solvent,
d) 0 to 25% by weight of at least one colorant, and
e) 0 to 25% by weight of at least one further additive,
wherein the sum of components a) to e) adds up to 100%.

The printing ink formulations according to the invention are advantageously prepared in a conventional manner, for example by mixing the individual components. As mentioned earlier, the new crystal form of compound (1) is present in the printing ink formulations in a dissolved or finely divided solid form. Additional colorants may be employed in the printing ink formulation of the invention or in a separate ink formulation. When additional colorants are to be employed in a separate formulation, the time of application of the printing ink formulation according to the invention is usually immaterial. The printing ink formulation according to the invention can for example be applied first and then be overprinted with conventional printing inks. But it is also possible to reverse this sequence or, alternatively, to apply the printing ink formulation according to the invention in a mixture with conventional printing inks. In every case the prints are readable with suitable light sources.

Primers can be applied prior to the printing ink formulation according to the invention. By way of example, the primers are applied in order to improve adhesion to the substrate. It is also possible to apply additional printing lacquers, e.g. in the form of a covering to protect the printed image. Additional printing lacquers may also be applied to serve aesthetic purposes, or serve to control application-related properties. By way of example, suitably formulated additional printing lacquers can be used to influence the roughness of the surface of the substrate, the electrical properties, or the water-vapour-condensation properties. Printing lacquers are usually applied in-line by means of a lacquering system on the printing machine employed for printing the printing ink formulation according to the invention.

The printing ink formulations according to the invention are also suitable for use in multilayer materials. Multilayer materials are e.g. composed of two or more plastics foils, such as polyolefin foils, metal foils, or metallised plastics foils, which are bonded to one another, by way of example, via lamination or with the aid of suitable laminating adhesives. These composites may also comprise other functional layers, such as odour-barrier layers or water-vapour barriers.

The new crystal form of compound (1) and IR absorber mixtures are also especially suitable for laser welding of plastics.

The laser welding is preferably carried out using an ND:YAG laser at 1064 nm or using a diode laser at 980 nm or 940 nm. The concentration of the new crystal form of compound (1) or an IR absorber mixtures is e.g. from 5 to 500 ppm, preferably from 10 to 200 ppm.

In laser welding, plastics components are welded to one another. The plastics components to be fused may have any shape. For example, at least one of the plastics components may be a film.

The new crystal form of compound (1) is suitable for welding transparent at least translucent plastics materials. The employed plastics materials may be colourless or coloured. In principle, the plastics components to be fused may be composed of the same polymer or of different polymers. Preferably, the plastics components employed for laser welding are selected from thermoplastic polymers. However, it is also possible that neither of the plastics components to be fused is composed of thermoplastic; however, a coating of at least one part with a thermoplastic comprising the new crystal form of compound (1) is required.

The plastics components employed for laser welding preferably comprise or consist of at least one polymer selected from polyolefins, polyolefin copolymers, polytetrafluoroethylenes, ethylene-tetrafluoroethylene copolymers, polyvinyl chlorides, polyvinylidene chlorides, polyvinyl alcohols, polyvinyl esters, polyvinyl alkanals, polyvinyl ketals, polyamides, polyimides, polycarbonates, polycarbonate blends, polyesters, polyester blends, poly(meth)acrylates, poly(meth)acrylate-styrene copolymer blends, poly(meth)acrylate-polyvinylidene difluoride blends, polyurethanes, polystyrenes, styrene copolymers, polyethers, polyether ketones and polysulfones and mixtures thereof.

Preference is given to matrix polymers from the group of the polyolefins, polyolefin copolymers, polyvinyl alkanals, polyamides, polycarbonates, polycarbonate-polyester blends, polycarbonate-styrene copolymer blends, polyesters, polyester blends, poly(meth)acrylates, poly(meth)acrylate-styrene copolymer blends, poly(meth)acrylate-polyvinylidene difluoride blends, styrene copolymers and polysulfones and mixtures thereof.

Particularly preferred polymers are transparent or at least translucent. Examples include: polypropylene, polyvinylbutyral, nylon-[6], nylon-[6,6], polycarbonate, polycarbonate-polyethylene terephthalate blends, polycarbonate-polybutylene terephthalate blends, polycarbonate-acrylonitrile/styrene/acrylonitrile copolymer blends, polycarbonate-acrylonitrile/butadiene/styrene copolymer blends, polymethyl methacrylate-acrylonitrile/butadiene/styrene copolymer blends (MABS), polyethylene terephthalate, polybutylene terephthalate, polymethyl methacrylate, impact-modified polymethyl methacrylate, polybutyl acrylate, polymethyl methacrylate-polyvinylidene difluoride blends, acrylonitrile/butadiene/styrene copolymers (ABS), styrene/acrylonitrile copolymers (SAN), polyphenylenesulfone and mixtures comprising 2 or more (e.g. 2, 3, 4, 5) of the afore-mentioned polymers.

Suitable polymer preparations for laser welding comprise
A) a thermoplastic matrix polymer suitable for forming the plastics parts,
B) the new crystal form of compound (1) as defined before,
C) optionally at least one further additive.

Those polymer preparations for laser welding are likewise in accordance with the invention and are suitable for producing fusion-bonded plastics parts with the aid of laser radiation whose wavelength is outside the visible region.

Polymer preparations for laser welding may advantageously be produced by a conventional extrusion or kneading process. The components B), and, if present, C) may be mixed from the outset, in the weight ratio corresponding to the desired end concentration, with the matrix polymer A) (direct compounding), or a distinctly higher concentration of B) and, if present, C) may initially be selected and the concentrate formed (masterbatch) subsequently diluted with further matrix polymer A) in the course of the manufacture of the parts to be fused.

Suitable additives C) are UV stabilizers, antioxidants, processing plasticizers, etc.

In addition, the polymer preparations for laser welding may comprise at least one colorant for establishing a desired hue as additive, especially transparent organic pigments and in particular dyes, for example C.I. Pigment Yellow 109, 110, 128, 138, 139, 150, 151, 147, 180, 183, 185 192 and 196, C.I. Pigment Orange 70, C.I. Pigment Red 122, 149, 178 and 179, 181, 202, 263, C.I. Pigment Violet 19, 23, 37 and 29, C.I. Pigment Blue 15, 15:1, 15:3 and 15:4, 60, C.I. Pigment Green 7 and 36, C.I. Solvent Yellow 14, 21, 93, 130, 133, 145, 163, C.I. Solvent Red 52, 135, 195, 213, 214 and 225, C.I. Solvent Blue 35, 45, 67, 68, 97, 104, 122, 132, C.I. Solvent Violet 13, 46, 49, C.I. Solvent Green 3, 5 and 28, C.I. Solvent Orange 47, 60, 86, 114, and 163, C.I. Solvent Brown 35, 53, and also C.I. Disperse Yellow 54, 87, 201, C.I. Disperse Orange 30, C.I. Disperse Red 60 and C.I. Disperse Violet 57.

A further possible additive group is that of additives which likewise modify the visual appearance, the mechanical properties or else the tactile properties, for example matting agents, such as titanium dioxide, chalk, barium sulfate, zinc sulfide, fillers, such as nanoparticulate silicon dioxide, aluminium hydroxide, clay and other sheet silicates, glass fibers and glass spheres.

The following examples illustrate the invention without restricting it.

EXAMPLES

X-Ray Powder Diffraction Method:

Conditions for obtaining powder X-ray diffraction (XRD) patterns: The powder x-ray diffraction patterns were obtained by methods known in the art using PANanalytical X-pert Pro diffractometer with X'Celerator detector using CuKα radiation (tube operating at 45 kV and 40 mA) in the Bragg-Brentano (reflection) geometry. Data were recorded from 3,006 to 35,006° 2θ in steps of 0,0167113° 2θ and the measurement time of 19,050 seconds per step. Variable divergence and antiscatter slits were used to maintain 5 mm of sample length irradiated.

Comparative Example 1

Preparation of Form A of compound (1) (see Example 1 of WO2012/069518):

The compound is known from Eur. J. Inorg. Chem. 2003, 1939-1947 and its preparation is described therein.

1,3-Diphenyl-4,5-dioxo-imidazoline is reacted under reflux with metallic nickel and Lawesson's reagent in toluene.

Using chlorobenzene instead of toluene leads to a higher yield. Absorption maximum (chloroform): 1023 nm The obtained product (crystals) —in both cases—shows the PXRD pattern of Form A of compound (1). Reference is made to FIG. 1.

Example 2

Dry heating of the solids of compound (1) obtained in Comparative Example 1 (Form A of compound (1)) at 150° C. for 12 hours resulted in the new crystal form of compound (1) (Form B of compound (1)); detectable by measurement of its PXRD. Reference is made to FIG. 2.

Form B of compound (1) characterized by the following X-ray diffraction pattern:

| Scattering Angle (2 Theta) | d-spacing (Angstrom) | Relative Intensity (%) |
|---|---|---|
| 6.1 ± 0.2 | 14.5 ± 0.5 | 37.7 |
| 8.2 ± 0.2 | 10.8 ± 0.3 | 100.0 |
| 11.3 ± 0.2 | 7.8 ± 0.2 | 15.9 |
| 15.9 ± 0.2 | 5.6 ± 0.1 | 13.1 |
| 16.1 ± 0.2 | 5.5 ± 0.1 | 11.5 |
| 17.9 ± 0.2 | 4.9 ± 0.1 | 22.8 |

Example 3

46 g of the solids of compound (1) obtained in Comparative Example 1 (Form A of compound (1)) were suspended in 3 l of chlorobenzene. The mixture was refluxed for 2 h, cooled to 50° C., filtered, washed with acetone, and dried, to obtain 43.5 g of the new crystal form of compound (1) (Form B of compound (1)).

Anal. Calculated for $C_{30}H_{20}N_4NiS_6$: C, 52.40; H, 2.93; N, 8.15; Ni, 8.54; S, 27.98. Found: C, 51.8; H, 2.9; N, 8.0; Ni, 8.9; S, 27.9.

Example 4

1.22 g of the solids of compound (1) obtained in Comparative Example 1 (Form A of compound (1)) were suspended in 100 mL of 3-methoxypropanenitrile. The mixture was refluxed for ¼ h, cooled to 14° C., filtered, washed with acetone, and dried, to obtain 1.10 g of the new crystal form of compound (1) (Form B of compound (1)).

Anal. Calcd for $C_{30}H_{20}N_4NiS_6$: C, 52.40; H, 2.93; N, 8.15; Ni, 8.54; S, 27.98. Found: C, 52.5; H, 2.9; N, 8.1; Ni, 8.5; S, 27.7.

Application Example 1

An offset ink absorbing IR radiation is prepared containing 10 weight percent on solids of form (B) of compound (1). The ink is prepared on a 3-roll mill and comprises 90 weight percent of a commercial offset varnish. The ink is printed by an offset printing equipment on paper (APCO II/II, Fogra). The print is clearly visible in the IR range using an IR-viewing device (cut-off filter 715 nm).

Application Example 2

An offset ink absorbing IR radiation is prepared containing 10 weight percent on solids of form (B) of compound (1). The ink is prepared on a 3-roll mill and comprises 90 weight percent of a commercial offset varnish. The ink is printed by an offset printing equipment on diacetate film (Rachow Kunststoff-Folien Gmbh). The print is clearly visible in the IR range using an IR-viewing device (cut-off filter 715 nm).

Compound (1) contained in the printed product—in both cases—shows the PXRD pattern of Form B of compound (1).

The invention claimed is:

1. A crystal form of bis(diphenylimidazolidinetrithione-κS4, κS5)-, (SP-4-1)-nickel(II) (compound (1)), characterized in an X-ray diffraction pattern by diffraction peaks corresponding to two theta scattering angles of 6.1; 8.2; 11.3; 15.9; 16.1 and 17.9.

2. A process, comprising employing the crystal form of the compound (1) according to claim 1, as IR absorber for security printing, invisible IR bar codes or IR readable bar codes, laser-welding of plastics, curing of surface-coatings using IR radiators, drying and curing of print, fixing of toners on paper or plastics, optical filters for plasma display panels, laser marking of paper or plastics, heating of plastics preforms, in 3D printing, in optical sensors or for heat shielding applications.

3. A printing ink formulation for security printing, comprising
   a) the crystal form of compound (1) according to claim 1,
   b) a polymeric binder,
   c) a solvent,
   d) optionally at least one colorant, and
   e) optionally at least one further additive.

4. The printing ink formulation according to claim 3, comprising
   a) 0.0001 to 25% by weight of the crystal form of compound (1),
   b) 5 to 74% by weight of at least one polymeric binder,
   c) 1 to 94.9999% by weight of at least one solvent,
   d) 0 to 25% by weight of at least one colorant, and
   e) 0 to 25% by weight of at least one further additive,
   wherein the sum of components a) to e) adds up to 100%.

5. A security document, comprising a substrate and the crystal form of compound (1) according to claim 1.

6. A security document, obtained by a printing process, wherein the printing ink formulation according to claim 3 is employed.

7. The security document according to claim 5, wherein the security document is selected from the group consisting of a bank note, a passport, a check, a voucher, an ID- or transaction card, a stamp and a tax label.

8. A process for producing the crystal form of compound (1) according to claim 1, comprising:
   heating a crystal form of compound (1), which is characterized in an X-ray diffraction pattern by diffraction peaks corresponding to two theta scattering angles of 7.4; 8.0 and 18.3, at 150° C. for 12 hours.

9. A process for producing the crystal form of compound (1) according to claim 1, comprising:
   heating a suspension of the crystal form of compound (1), which is characterized in an X-ray diffraction pattern by diffraction peaks corresponding to two theta scattering angles of 7.4; 8.0 and 18.3, in a solvent at reflux for 5 minutes to 12 hours.

10. The process according to claim 9, wherein the solvent is chlorobenzene and the suspension is refluxed for 2 hours.

11. The process according to claim 9, wherein the solvent is 3-methoxypropanenitrile and the suspension is refluxed for ¼ hours.

12. A method of detecting the authenticity of the security document according to claim 5, comprising:

a) measuring an absorbance, reflectance or transmittance spectrum of the security document in the VIS/NIR range of the electromagnetic spectrum; and
b) comparing the spectrum measured under a) and/or information derived therefrom with a corresponding spectrum and/or information of an authentic security element.

* * * * *